United States Patent [19]
Bowne et al.

[11] Patent Number: 4,892,805
[45] Date of Patent: Jan. 9, 1990

[54] PHOTOGRAPHIC ELEMENT AND PROCESS

[75] Inventors: Arlyce T. Bowne; Robert F. Romanet, both of Rochester; Sharon E. Normandin, Macedon, all of N.Y.

[73] Assignee: Eastman Kodak Company, Rochester, N.Y.

[21] Appl. No.: 265,197

[22] Filed: Oct. 31, 1988

[51] Int. Cl.$^4$ ................................. G03C 7/38
[52] U.S. Cl. .................... 430/387; 430/386; 430/558
[58] Field of Search .................. 430/558 R, 386, 387

[56] References Cited

U.S. PATENT DOCUMENTS

| | | | |
|---|---|---|---|
| 4,443,536 | 4/1984 | Lestina | 430/552 |
| 4,540,654 | 9/1985 | Sato et al. | 430/558 |
| 4,559,297 | 12/1985 | Seto et al. | 430/551 |
| 4,639,413 | 1/1987 | Kawagishi et al. | 430/546 |
| 4,639,415 | 1/1987 | Kaneko et al. | 430/551 |
| 4,665,015 | 5/1987 | Iijima et al. | 430/543 |

FOREIGN PATENT DOCUMENTS

| | | | |
|---|---|---|---|
| 0284239 | 9/1988 | European Pat. Off. | |
| 0284240 | 9/1988 | European Pat. Off. | |
| 0285274 | 10/1988 | European Pat. Off. | |
| 1252418 | 11/1968 | United Kingdom | 430/555 |
| 1247493 | 9/1971 | United Kingdom | 430/476 |
| 1398979 | 6/1975 | United Kingdom | 430/548 |

*Primary Examiner*—Richard L. Schilling
*Attorney, Agent, or Firm*—Richard E. Knapp

[57] ABSTRACT

Novel pyrazoloazole dye-forming couplers containing at least one polyether group (A) comprising at least three ether (—O—) groups and terminated by a hydroxy, carboxy or sulfonamido group enables increased reactivity of the coupler in a photographic element and process. The couplers are useful in color photographic silver halide materials and processes.

8 Claims, No Drawings

PHOTOGRAPHIC ELEMENT AND PROCESS

This invention relates to novel pyrazoloazole dye-forming couplers and to photographic silver halide elements and processes using such couplers.

Color images are customarily obtained in the photographic art by reaction between the oxidation product of a silver halide developing agent and a dye-forming coupler. Pyrazolone couplers are useful for forming magenta dye images; however, pyrazoloazole couplers, particularly pyrazolotriazole couplers, represent another class of couplers that are useful for this purpose. Examples of pyrazolotriazole couplers are described in, for example, U.S. Pat. No. 4,443,536; U.K. Patents 1,247,493; 1,252,418; and 1,398,979; and U.S. Pat. Nos. 4,665,015, 4,639,415; 4,639,413; and 4,559,297. An example of such a pyrazolotriazole coupler is represented by the formula:

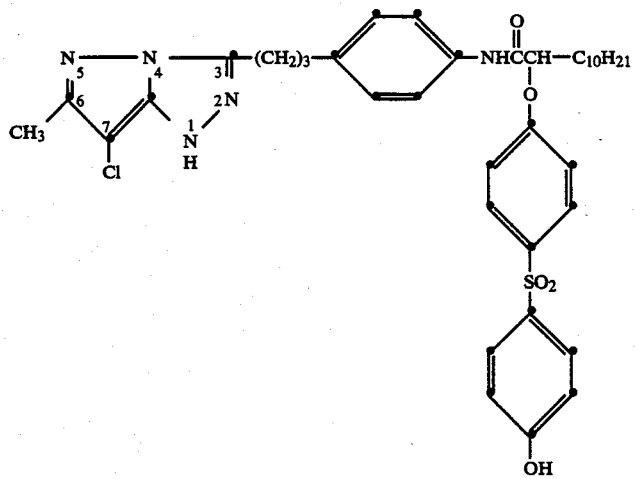

While such magenta dye-forming couplers are useful in photographic silver halide materials and processes, many of such couplers in photographic silver halide elements and processes do not provide optimum dye images. It has been desirable to provide a pyrazoloazole coupler that enables increased pyrazoloazole coupler reactivity, that is, such a coupler that enables increased magenta image-dye density.

It has been found that a novel dye-forming pyrazoloazole coupler enabling the described advantages comprises at least one polyether group (A) comprising at least three ether (—O—) groups and terminated by a hydroxy, carboxy, or sulfonamido group. Such a coupler upon reaction with an oxidized color developing agent forms a dye in a photographic silver halide element. These couplers are particularly useful to provide increased photographic activity as demonstrated by the increased maximum dye density provided and also provide increased light stability.

Such dye-forming couplers are particularly useful incorporated in color photographic silver halide materials and processes. These couplers are useful for forming magenta dye images.

Pyrazolotriazoles are particularly useful pyrazoloazoles as described. Such pyrazolotriazoles include, for example, pyrazolo[3,2-c]-s-triazole couplers. Such pyrazolotriazoles also include, for example, 1H-pyrazolo[2,3-b]-1,2,4-triazoles that can also be named as 1H-pyrazolo[1,5-b]-1,2,4-triazoles. The latter nomenclature has been used in the photographic art in, for example, U.S. Pat. No. 4,540,654. The polyether group (A) in the case of the pyrazolo[3,2-c]-s-triazoles is in the 3- and/or 6-position of the coupler, preferably in the 3-position. The polyether group (A) in the case of the pyrazolo[2,3-b]-1,2,4-triazoles is in the 2- and/or 6-position.

It is believed that the combination of changes in hydrophilicity of the coupler caused by the particular molecular structure of the coupler to a large extent contributes to the described advantages. With the increased hydrophilicity the coupler is more reactive; however, the degree of increased hydrophilicity is not sufficiently large to cause the coupler to cause adverse effects such as undesired dye mobility leading to loss of sharpness and color contamination of adjacent layers. The terminal group, particularly the hydroxy, carboxy or sulfonamido group on the polyether group (A) enables the coupler to have a satisfactory balance of properties, such as greater interaction with aqueous developers for enhanced dye-forming efficiency and sufficient immobility to avoid undesired migration into adjacent layers. If the terminal hydroxy group, for example, is replaced by an alkyl group, the described advantages are not observed. Also, if the polyether group has less than three ether (—O—) groups, the pyrazoloazole typically has less than sufficient hydrophilicity to enable the described advantages. Such advantages are observed in the couplers of the invention in addition to the advantages that pyrazoloazole couplers are known to provide in photographic silver halide materials, such as resistance to effects of formaldehyde.

Pyrazoloazole couplers as described preferably are pyrazolo[3,2-c]-s-triazoles having a polyether group in at least one of the 3- and 6-positions represented by the formula:

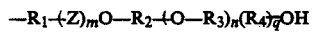

wherein $R_1$, $R_2$, $R_3$ and $R_4$ are individually unsubstituted or substituted alkylene, such as alkylene containing 1 to 25 carbon atoms, for example, methylene, propylene and butylene, or arylene, such as arylene containing 6 to 10 carbon atoms, such as phenylene or naphthylene; m and q are individually 0 or 1; n is 2 to 10; and, Z is —NHCOR$_5$— wherein R$_5$ is unsubstituted or substituted alkylene, such as alkylene containing 1 to 25 carbon atoms, for example, methylene, ethylene, propylene and butylene, or unsubstituted or substituted arylene, such as arylene containing 6 to 25 carbon atoms, for example, phenylene.

Examples of useful polyether groups with the described formula are:

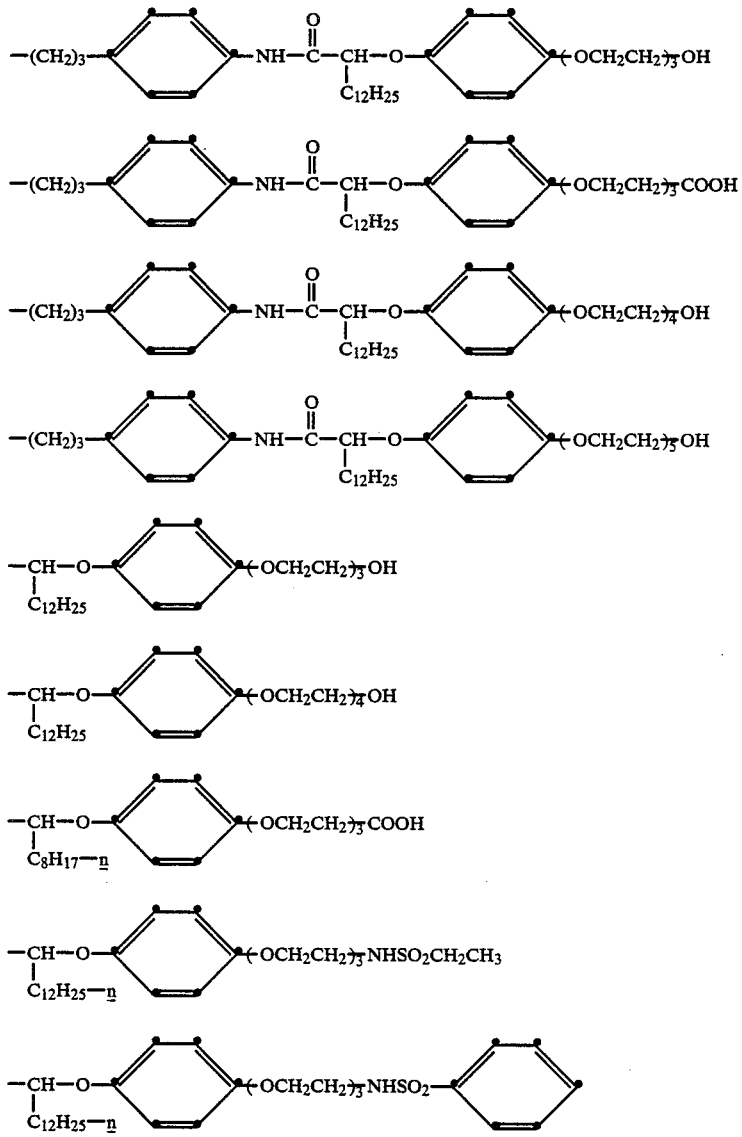

The pyrazoloazole coupler typically contains, in a position that does not contain the described polyether group (A), a hydrogen or group that typically promotes solubility, diffusion resistance or dye hue of the dye formed from the coupler upon reaction with oxidized color developing agent.

The pyrazoloazole coupler, typically the pyrazolo[3,2-c]-s-triazole coupler, contains, in a position not containing the polyether group (A), hydrogen or a group selected from the following: amino, such as dioctylamino, dimethylamino and dodecylamino; alkyl, such as alkyl containing 1 to 30 carbon atoms, for example, methyl, ethyl, propyl, n-butyl, t-butyl, octyl and eicosyl; cycloalkyl, such as cyclohexyl and cyclopentyl; aryl, such as aryl containing 6 to 20 carbon atoms, for example, phenyl, naphthyl, and mesityl; carboxy; cyano; nitro; a heterocyclic group, such as a heterocyclic group comprises of atoms selected from carbon, oxygen, nitrogen and sulfur atoms necessary to complete a five- or six-member ring, for example, furyl, pyrrolyl, thienyl, thiazolyl, oxazolyl and pyridyl; or —($L_1$-)$_n$—($L_2$)$_m$—$R_a$ wherein $L_1$ is a linking group that does not adversely affect the desired properties of the coupler, such as alkylene, for example, alkylene containing 1 to 20 carbon atoms, for example, methylene, ethylene, propylene, n-butylene, and octylene, or arylene, such as arylene containing 6 to 30 carbon atoms, for example, phenylene and naphthylene; $L_2$ is a linking group that does not adversely affect the desired properties of the coupler, and that is the same as or different from $L_1$, and is typically —O—, —S—, —CO—, —CO$_2$—, —SO$_2$—, —SO—, —NR$_7$SO$_2$NR$_8$—,

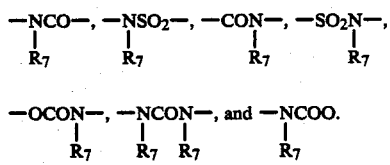

$R_7$ and $R_8$ are individually hydrogen, alkyl, such as alkyl containing 1 to 30 carbon atoms, for example, methyl, ethyl, propyl, n-butyl, t-butyl, and eicosyl, or aryl, such as aryl containing 6 to 30 carbon atoms, for example, phenyl and naphthyl; n and m are individually 0 or 1; and, $R_a$ is alkyl, such as alkyl containing 1 to 30 carbon atoms, for example, methyl, ethyl, propyl, n-butyl, t-butyl, and octyl, or aryl, such as aryl containing 1 to 30 carbon atoms, for example, phenyl, naphthyl and mesityl; or a heterocyclic group, for example, a five- or six-member heterocyclic group comprised of atoms selected from carbon, oxygen, nitrogen and sulfur atoms, such as oxazole, pyridine, pyrrole and thiophene rings.

These groups are unsubstituted or substituted with groups that do not adversely affect the desired properties of the pyrazoloazole coupler. Examples of useful substituents include ballast groups and coupler moieties known to be useful in the photographic art, or alkyl containing 1 to 4 carbon atoms, such as methyl, ethyl, propyl, n-butyl and t-butyl.

The pyrazoloazole contains in the coupling position, hydrogen or a coupling-off group, also known as a leaving group.

Coupling-off groups, defined by Z herein, are well known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U.K. patents and published application numbers 1,466,728; 1,531,927; 1,533,039; 2,006,755A and 2,017,704A; the disclosures of which are incorporated herein by reference.

Examples of specific coupling-off groups are

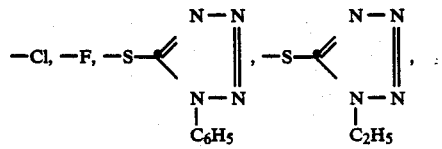

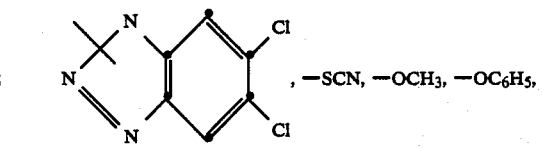

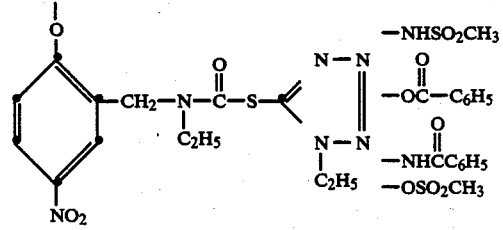

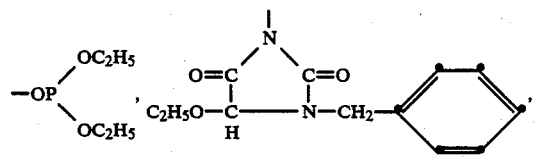

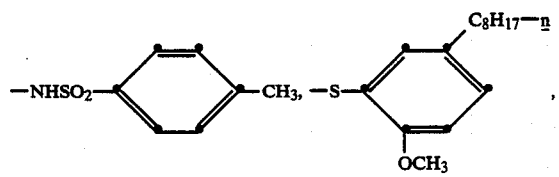

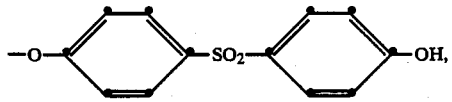

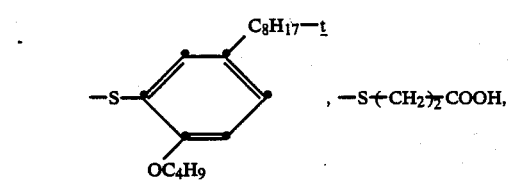

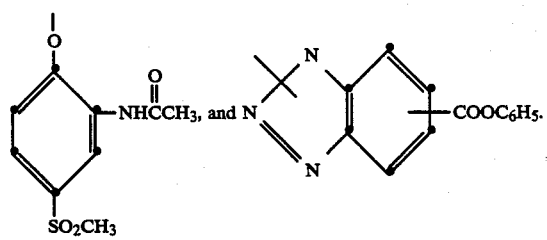

The pyrazoloazoles typically comprise a ballast group. A ballast group as described is an organic radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups on the pyrazoloazole nucleus. For example, one or more coupler moieties can be attached to the same ballast group. Representative ballast groups include substituted or unsubstituted alkyl or aryl groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms, respectively, can be further substituted with such substituents.

Particularly useful pyrazoloazole couplers are those that comprise a water-solubilizing group for some photographic materials that enables increased reactivity of the coupler. For example, a particularly useful coupler is a pyrazoloazole, as described, comprising a substituent, such as a ballast group, comprising at least one carboxy group.

Illustrative pyrazoloazole couplers are represented by the formula:

COUP—(A)

wherein COUP is a pyrazoloazole coupler nucleus and (A) is a polyether group as described.

Preferred pyrazoloazole couplers as described are pyrazolo[3,2-c]-s-triazoles represented by the formula:

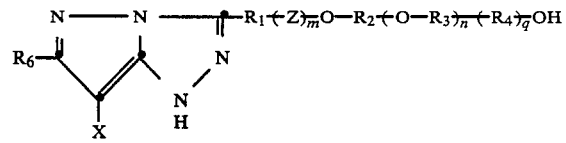

wherein
X is hydrogen or a coupling-off group;
$R_1$, $R_2$, $R_3$ and $R_4$ are individually unsubstituted or substituted alkylene or arylene, such as alkylene containing 1 to 25 carbon atoms, for example, methylene, ethylene, propylene and butylene, or arylene containing 6 to 25 carbon atoms, such as phenylene or naphthylene;
m and q are individually 0 or 1:
n is 2 to 6, preferably 2 to 4;
Z is a linking group, preferably —$NHCOR_5$ wherein $R_5$ is unsubstituted or substituted alkylene or arylene, as described; and,
$R^6$ is unsubstituted or substituted alkyl or aryl, as described.

Examples of preferred couplers are:

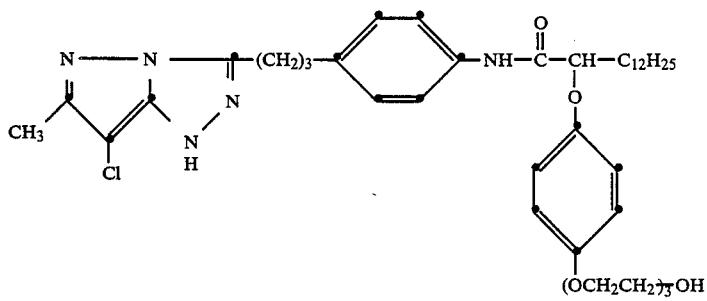

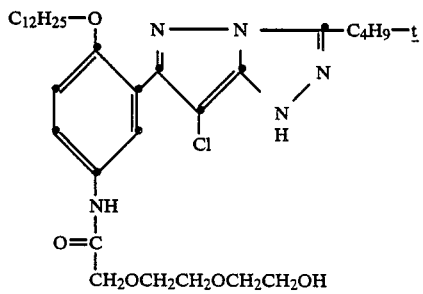

-continued

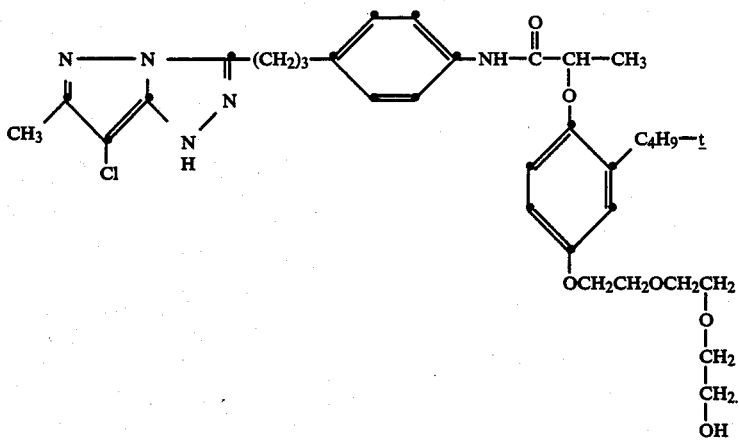

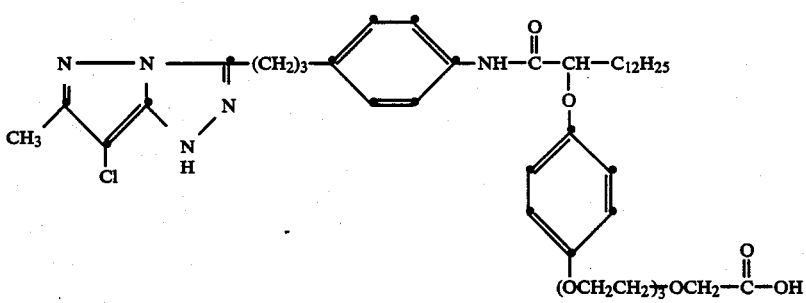

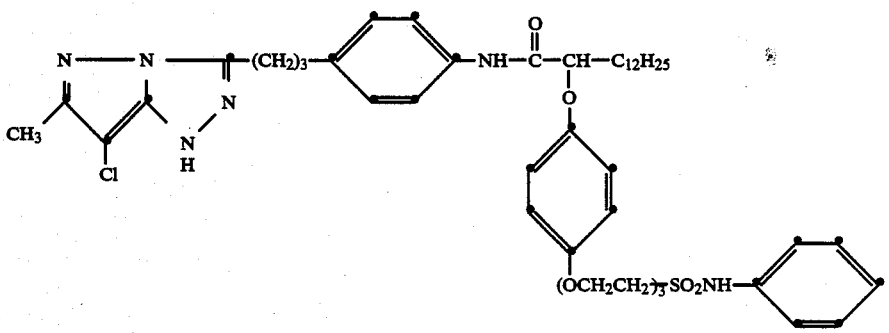

Pyrazoloazole couplers according to the invention can be used in ways and for purposes that pyrazoloazole couplers have been used in the photographic art.

Pyrazoloazole couplers, particularly pyrazolotriazole couplers, according to the invention can be prepared by the general methods of synthesis described in the art, such as in Research Disclosure, August 1974, Item No. 12443, published by Kenneth Mason Publications, Ltd., The Old Harbourmaster's, 8 North Street, Emsworth, Hampshire PO10 7DD, England and U.S. Pat. No. 4,540,654. An illustrative synthetic scheme for preparation of couplers according to the invention is as follows:

The compounds of the invention can be made by known synthetic routes. Typically, the pyrazolotriazole with a linking group ($L^1$) containing an amine is reacted with a ballast acid chloride containing the polyether group as illustrated in the following reaction:

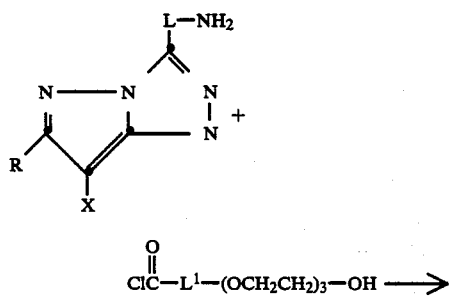

-continued

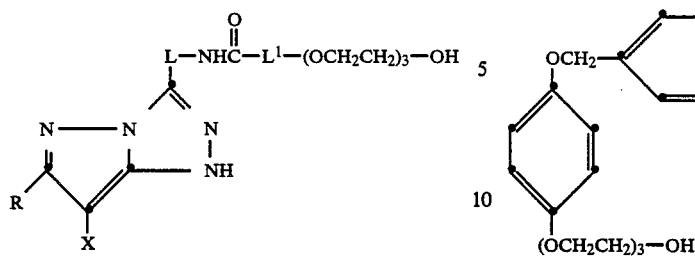

wherein X is a coupling-off group; L is a linking group; L¹ is an optional linking group that is the same as or different from L; and R is a substituent group.

The synthesis of a typical example is as follows:

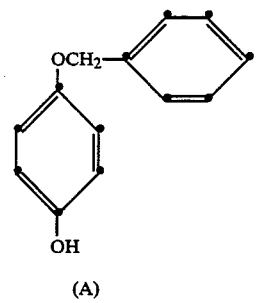

(A)

+

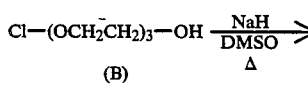

(B)

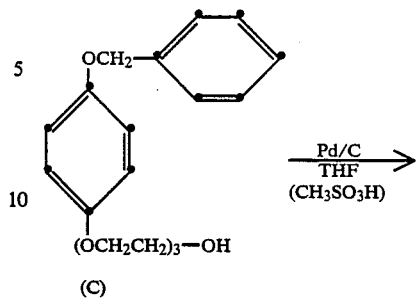

(C)

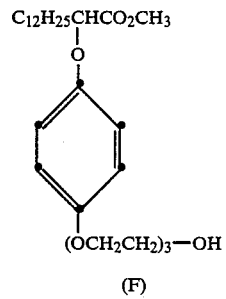

(D)

Starting material (4.2 g, 0.017 mol) was hydrogenated on a Parr shaker for one hour with 2 gm Pd on carbon and two drops $CH_3SO_3H$ in 100 mL THF (tetrahydrofuran). The solution was filtered and evaporated to solid (D) and used as is.

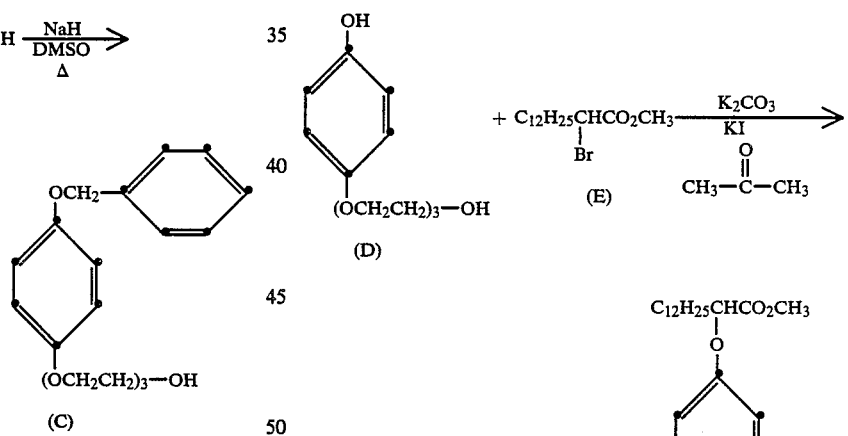

The phenol (8.4 g, 0.059 mol) (A) was added to 2.4 g (0.059 mol) of a 50% dispersion of NaH (washed in hexane), in 100 mL DMSO (dimethylsulfoxide) and stirred at ambient temperature (20° C.) for ½ hour. The chloro compound (10.0 g, 0.059 mol) (B) was added and the mixture heated to 100° C. for 2 hours. The reaction was cooled and added to dilute HCL and ethyl acetate was added. The organic layers were washed several times with water, dried with $MgSO_4$, and evaporated to 12.0 g of an oil. Chromatography on silica gel with ether gave 9.0 g white solid. Nmr was consistent with structure.

3.0 g of starting phenol (0.0116 mol) (D), 3.73 g (0.0116 mol) of the bromo ester (E), 4.8 g (0.034 mol) $K_2CO_3$, and 0.15 g (0.00116 mol) KI were refluxed in acetone overnight, cooled and filtered. After evaporation of the solvent, the residue was taken up in ethyl acetate and washed with water, dried with $MgSO_4$, and evaporated. It was then chromatographed with a $CH_3CH_2OCH_2CH_3/CH_2Cl_2$ mixture on silica gel to obtain 3.9 g product.

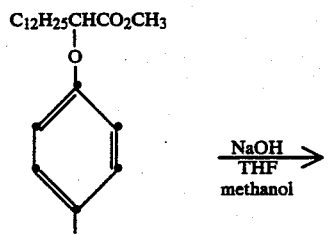

(F)

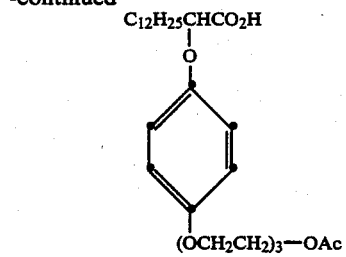

3.8 g (0.0081 mol) acid was stirred with 1.3 mL (0.0182 mol) acetyl chloride in 25 mL THF overnight forming Compound 1. It was evaporated to an oil and used as is.

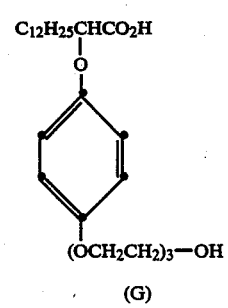

(G)

3.9 ester was dissolved in 20 mL THF and 20 mL methanol and 5 ml 50% NaOH solution added. After stirring 5 minutes, it was poured into cold HCl, ethyl acetate was added, and the organic layer washed with water, dried with MgSO₄, and evaporated.

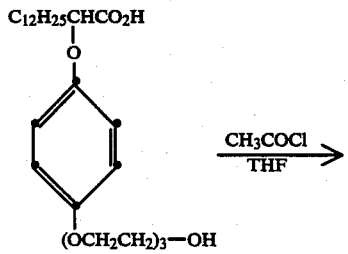

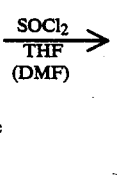

(F)

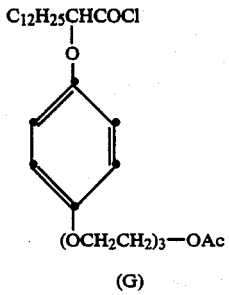

(G)

The product from the previous reaction was refluxed ½ hour with 5 mL SOCl₂, 5 mL THF and 2 drops DMF (dimethylformamide). It was then evaporated to an oil and used immediately.

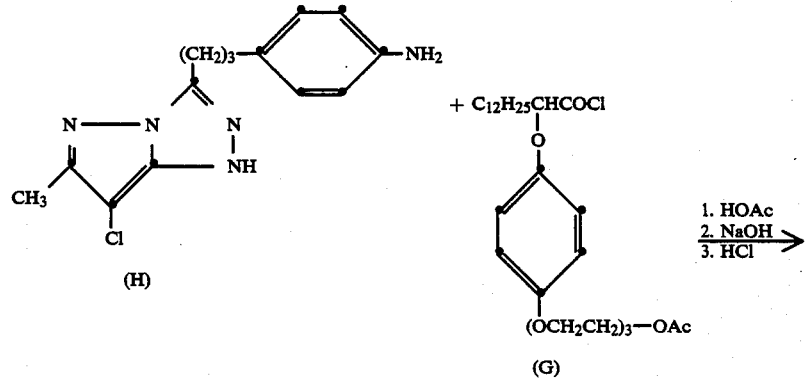

-continued

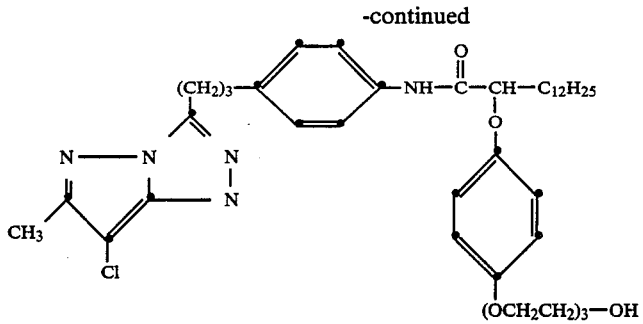

The amine (H) was suspended in HOAc and brought to reflux. After cooling to 40° C. the acid chloride (G) was added and the reaction stirred at ambient temperature (20° C.) for 2 hours. It was added to water, ethyl acetate added, and the organic layer washed, dried, and evaporated. The residue taken up in 5 mL methanol and 5 mL THF and made pH14 with 2N NaOH and stirred 15 minutes. It was added to dilute HCl, ethyl acetate was added and the organic layer washed, dried, and evaporated. The product was chromatographed on silica gel, with ether. Nmr and analysis were consistent with the pyrazolotriazole according to the invention.

The couplers of this invention can be incorporated in silver halide emulsions and the emulsions can be coated on a support to form a photographic element. Alternatively, at least one of the couplers can be incorporated in photographic elements adjacent the silver halide emulsion where, during development, the coupler will be in reactive association with development products such as oxidized color developing agent.

The photographic elements can be either single color or multicolor elements. In a multicolor element, the magenta dye-forming coupler is usually associated with a green-sensitive emulsion, although they could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler, a magenta image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the elements of this invention, reference will be made to *Research Disclosure*, December 1978, Item 17643, published by Kenneth Mason Publications, Ltd., The Old Harbourmaster's, 8 North Street, Emsworth, Hampshire PO10 7DD, ENGLAND, the disclosures of which are incorporated herein by reference. This publication will be identified hereafter by the term "*Research Disclosure*."

The silver halide emulsions employed in the elements of this invention can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al. U.S. Pat. No. 4,434,226, Daubendiek et al. U.S. Pat. No. 4,414,310, Wey U.S. Pat. No. 4,399,215, Solberg et al. U.S. Pat. No. 4,433,048, Mignot U.S. Pat. No. 4,386,156, Evans et al. U.S. Pat. No. 4,504,570, Maskasky U.S. Pat. No. 4,400,463, Wey et al. U.S. Pat. No. 4,414,306, Maskasky U.S. Pat. Nos. 4,435,501 and 4,643,966 and Daubendiek et al. U.S. Pat. Nos. 4,672,027 and 4,693,964. Also specifically contemplated are those silver bromoiodide grains with a higher molar proportion of iodide in the core of the grain than in the periphery of the grain, such as those described in GB 1,027,146; JA 54/48,521; U.S. No. 4,379,837; U.S. No. 4,444,877; U.S. No. 4,665,012; U.S. No. 4,686,178; U.S. No. 4,565,778; U.S. No. 4,728,602; U.S. No. 4,668,614; U.S. No. 4,636,461; EP 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surfaces of the silver halide grains, or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated. Typical chemical sensitizers are listed in *Research Disclosure*, Item 17643, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls, and streptocyanines. Illustrative spectral sensitizing dyes are disclosed in *Research Disclosure*, Item 17643, cited above, Section IV.

Suitable vehicles for the emulsion layers and other layers of elements of this invention are described in Research Disclosure Item 17643, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section X), coating aids (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulfonamido)-ethylaniline sulfate hydrate, 4-amino-3-methyl-N-ethyl-N-$\beta$-hydroxyethylaniline sulfate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonic acid.

With negative-working silver halide, the processing step described above provides a negative image. The described elements are preferably processed in the known C-41 color process as described in, for example, the British Journal of Photography Annual of 1982, pages 209–211. To provide a positive (or reversal) image, the color development step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The following examples are included for a further understanding of the invention:

EXAMPLE 1

(Photographic Elements Comprising Pyrazoloazole Couplers of the Invention)

Photographic elements were prepared by coating a cellulose acetate-butyrate film support with a photosensitive layer containing a silver bromoiodide emulsion at 0.91 gm Ag/m$^2$, gelatin at 3.77 gm/m$^2$, and one of the couplers designated in Table I dispersed in half its weight of tricresyl phosphate and coated at 1.62 mmol/m$^2$. The photosensitive layer was overcoated with a layer containing gelatin at 1.08 gm/m$^2$ and bis-vinylsulfonylmethyl ether at 1.75 weight percent based on total gelatin.

Samples of each element were imagewise exposed through a graduated-density test object and processed at 40° C. employing the following color developing solution, then stopped, bleached, fixed washed, and dried to produce stepped magenta dye images.

| | |
|---|---|
| K$_2$SO$_3$ | 2.0 gm |
| K$_2$CO$_3$ | 30.0 gm |
| KBr | 1.25 gm |
| KI | 0.6 gm |
| 4-amino-3-methyl-N—ethyl-N—B'—hydroxyethylaniline sulfate | 3.55 gm |
| Water to 1.0 liter, pH 10.0 | |

The produced magenta dye images were evaluated by several tests and measurements, as shown in Table II. Densitometry of these images provided measures of maximum density (D$_{max}$) and contrast (gamma). Accelerated keeping tests on the dye image of initial density close to 1.5 gave the reported magenta density changes under the following conditions:

LF=6 week light fading under 5.4 klux xenon simulated average north skylight.

WO=6 week "wet oven" dark keeping, 60° C./70% RH.

TABLE I

C-1 (Comparative Coupler)

TABLE I-continued

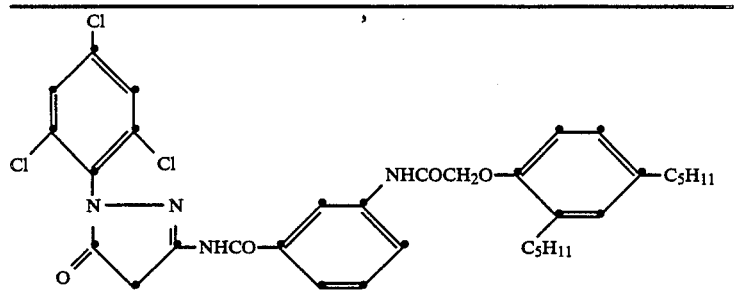

C-2 (Comparative Coupler)

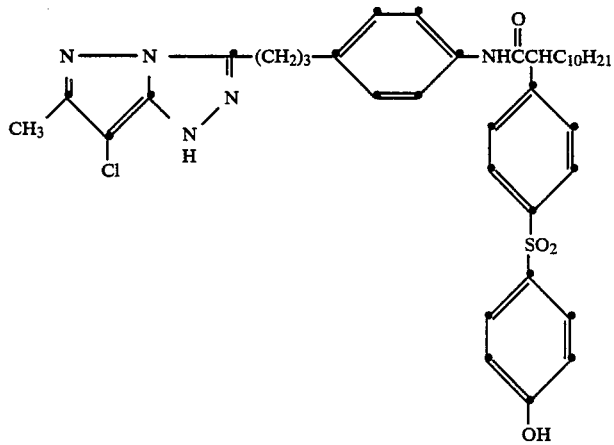

1 (Invention)

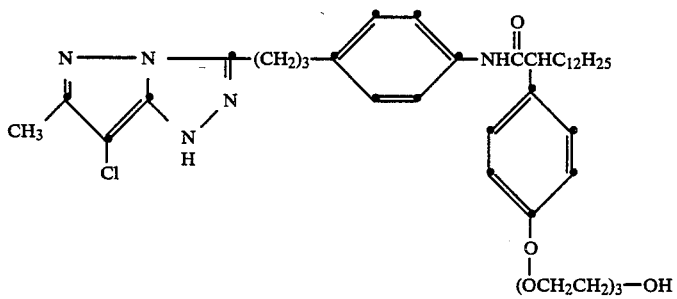

TABLE II

| Coupler | Comparison or Invention | Dmax | Gamma | WO | LF |
|---------|------------------------|------|-------|-----|-----|
| C-1 | Comparison | 2.53 | 0.77 | −25 | −69 |
| C-2 | Comparison | 3.55 | 1.17 | +2 | −82 |
| 1 | Invention | 2.94 | 1.03 | +2 | −35 |

The compound of the invention provides not only good photographic activity with high Dmax and gamma, but superior dye stabilities under dark and light keeping conditions compared to couplers C-1 and C-2.

The invention has been described in detail with particular reference to preferred embodiments thereof, but it will be understood that variations and modifications can be effected within the spirit and scope of the invention.

What is claimed is:

1. A photographic element comprising a support bearing a photographic silver halide emulsion and a dye-forming coupler wherein the dye-forming coupler is a pyrazoloazole coupler comprising at least one polyether group (A) comprising at least three ether (—O—) groups and terminated by a hydroxy carboyx, or sulfonamido group.

2. A photographic element as in claim 1 wherein the pyrazoloazole coupler is a pyrazolo[3,2-c]-s-triazole having a polyether group in the 3- or 6-position represented by the formula:

$$-R_1+Z)_mO-R_2+O-R_3)_n(R_4)_qOH$$

wherein
$R_1$, $R_2$, $R_3$ and $R_4$ are individually unsubstituted or substituted alkylene or arylene;
m and q are individually 0 or 1;
n is 2 to 10; and, $$Z \text{ is } -NH\overset{O}{\overset{\|}{C}}-R_5-$$

wherein $R_5$ is unsubstituted or substituted alkylene or arylene.

3. A photographic element as in claim 1 wherein the polyether group (A) is represented by the formula:

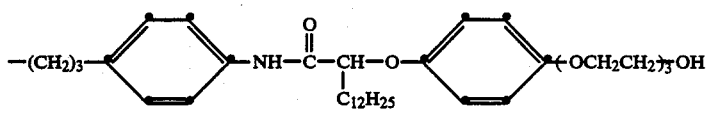

4. A photographic element as in claim 1 wherein the pyrazoloazole coupler is a pyrazolo[3,2-c]-s-triazole represented by the formula:

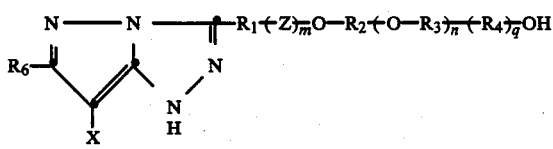

wherein
X is hydrogen or a coupling-off group;
$R_1$, $R_2$, $R_3$ and $R_4$ are individually unsubstituted or substituted alkylene or arylene;
m and q are individually 0 or 1;
n is 2 to 10;
Z is

wherein $R_5$ is unsubstituted or substituted alkylene or arylene; and
$R_6$ is unsubstituted or substituted alkyl or aryl.

5. A photographic element as in claim 1 wherein the pyrazoloazole coupler is a pyrazolotriazole represented by the formula:

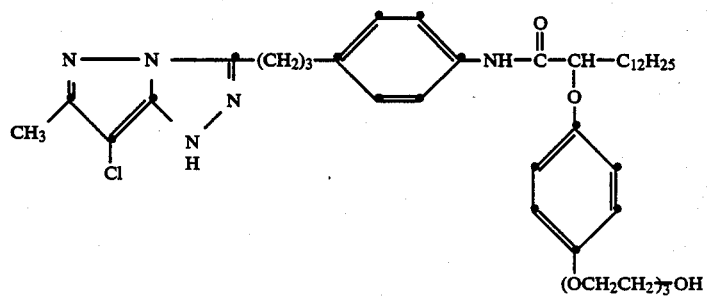

6. A process of forming a dye image in an exposed photographic element comprising a support bearing a photographic silver halide emulsion, said process comprising developing the photographic element with a silver halide color developing agent in the presence of a color coupler comprising a pyrazoloazole coupler comprising at least one polyether group (A) comprising at least three ether (—O—) groups and terminated by a hydroxy, carboxy or sulfonamide group.

7. A process as in claim 6 wherein the pyrazoloazole coupler is a pyrazolo[3,2-c]-s-triazole having a polyether group in the 3- or 6-position represented by the formula:

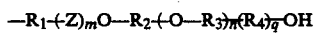

wherein
$R_1$, $R_2$, $R_3$ and $R_4$ are individually unsubstituted or substituted alkylene or arylene;
m and q are individually 0 or 1;
n is 2 to 10; and,

wherein $R_5$ is unsubstituted or substituted alkylene or arylene.

8. A process as in claim 6 wherein the pyrazoloazole coupler is a pyrazolotriazole represented by the formula:

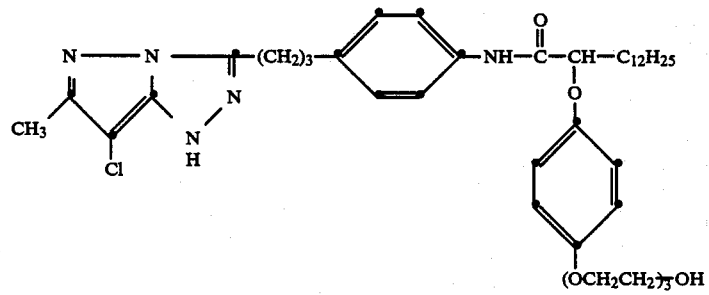

* * * * *

UNITED STATES PATENT AND TRADEMARK OFFICE
CERTIFICATE OF CORRECTION

PATENT NO.   : 4,892,805
DATED        : January 9, 1990
INVENTOR(S)  : Arlyce T. Bowne et al.

It is certified that error appears in the above-identified patent and that said Letters Patent is hereby corrected as shown below:

Column 4, line 3, "comprises" should be --comprised--.

Column 15, line 23, "dilue" should be --dilute--.

Column 20, line 50, "carboyx" should be --carboxy--.

Signed and Sealed this

Twentieth Day of August, 1991

Attest:

HARRY F. MANBECK, JR.

Attesting Officer      Commissioner of Patents and Trademarks